United States Patent [19]

Schenkel

[11] 4,389,402
[45] Jun. 21, 1983

[54] METHOD FOR THE CONTROL OF CATTLE GRUBS USING PENTADIENONE HYDRAZONES

[75] Inventor: Robert H. Schenkel, Yardley, Pa.

[73] Assignee: American Cyanamid Company, Stamford, Conn.

[21] Appl. No.: 295,056

[22] Filed: Aug. 21, 1981

[51] Int. Cl.³ .................... A61K 31/505; A61K 31/55
[52] U.S. Cl. .................................... 424/251; 424/244; 424/273 R; 424/326
[58] Field of Search ................ 424/326, 244, 251, 273

[56] References Cited

U.S. PATENT DOCUMENTS 4,087,525  5/1978  Lovell .................................. 424/244
4,163,102  7/1979  Lovell .................................. 424/251

*Primary Examiner*—Sam Rosen
*Attorney, Agent, or Firm*—American Cyanamid Co.

[57] ABSTRACT

Methods for protecting ruminant, domestic, and farm animals from parasitic infestations of the larvae of heel flies (cattle grubs) comprising oral or topical administration to host animals of a larvicidally effective amount of a pentadienone hydrazone.

6 Claims, No Drawings

METHOD FOR THE CONTROL OF CATTLE GRUBS USING PENTADIENONE HYDRAZONES

The invention herein described relates to methods for controlling larvae of flies in the family Hypodermatidae. These parasites, also known as ox warbles or cattle grubs, primarily infect ruminants (i.e., cattle, goats, sheep, etc.) but occasionally attack other domestic and farm animals or even humans. Susceptible host animals can be protected from infestations of parasitic cattle grubs by either topical or oral administration of a larvicidally effective amount of a pentadienone hydrazone.

By way of background, the chemicals utilized in the methods of the present invention are disclosed in the following U.S. Pats.: No. 4,087,525 (1978) and No. 4,163,102 (1979). pentadienone hydrazones are described by the patentee as effective insecticides and are particularly useful in controlling a variety of insects which attack important agricultural plants. However, these patents do not suggest that the compounds which are the subject of this invention are effective for controlling animal insect parasites which invade their hosts and damage or destroy flesh and/or hide. Utilizing pentadienones, methods are revealed in the present invention which demonstrate these compounds to be effective grubicidal agents useful for the protection of ruminants and other animals against attacks of the larvae of heel flies (cattle grubs or ox warbles).

Cattle grubs (or ox warbles) are the larvae of flies of the family Hypodermatidae, Genus Hypoderma (the heel flies). The best known species of this genus are: *Hypoderma linaeatum*, the common cattle grub, and *Hypoderma bovis*, the northern cattle grub; the former is widely distributed on the North American Continent, Europe and Asia, while the latter is less commonly distributed.

If host animals are in a standing position, heel fly parasites generally attach their eggs to the hairs on the legs of their hosts in the area from the hock to the knee. However, when the host animal is bedded down, the eggs may be attached to hairs on other parts of the animal's body which come in contact with the ground. The eggs usually hatch within a week, and the resulting fly larvae bore directly into the skin or hair follicles of their hosts. The larvae then work upward between the muscles, and in several months find their way into the abdominal and chest cavities of the host. During the next seven or eight months they continuously migrate over the surface of the paunch, intestines, spleen and other organs. Larvae appear to have a special affinity for the muscular and mucous layers of the esophagus and gullet, as they are generally found there in the greatest numbers when compared to other internal locations. In the fall, winter, and spring the grubs migrate through the muscular tissues of the back and reach a location under the surface of the skin. Final development of the grubs takes place under the hide on the animal's back, where the now rapidly developing grubs can be found in tumorous swellings which have breathing holes produced by the grubs. Fully developed larvae eventually emerge from the skin, drop to the ground and crawl into loose soil where they pupate and finally emerge as warble flies, thus completing the parasite's life cycle.

Injuries inflicted on animal hosts by parasitic larvae of the heel flies are of two general types: (1) significant irritation results from the burrowing of larvae through their host's tissues and subsequent emergence from the host's back; and (2) wounds produced by the emergence of larvae from the host's back attract tormenting insects (i.e., screw-worm flies).

Annual economic losses resulting from cattle grub infestations are estimated to be in the vicinity of one hundred million dollars. These losses are attributed to decreased milk production in dairy animals, weight loss and depreciation of flesh value in meat animals, destruction of hides, and even deaths caused by the aberrant wild behavior of animals in their efforts to escape from flies and the irritation caused by the parasitic larvae of heel flies.

Cattle grubs present a danger to people engaged in the care and handling of ruminants or other susceptible domestic and farm animals which serve as hosts for this parasite. Such individuals are frequently exposed to cattle grubs and may occasionally be infected. Humans contracting this disease may suffer long-term debilitating effects, or in some cases even death, as a result of the attack of these parasites.

In light of the foregoing discussions of impacts in the areas of animal husbandry and human health, control of cattle grubs is highly desirable. An object of this invention is to provide new and useful chemical methods for the control of this noxious parasite. This object is manifest in the following description and particularly delineated in the appended claims.

It has been discovered that pentadienone hydrazone compounds of this invention, when administered orally or topically to host animals, are highly effective grubicidal agents useful in the control of heel fly larvae. Such larvicidally-effective compounds have the following formula:

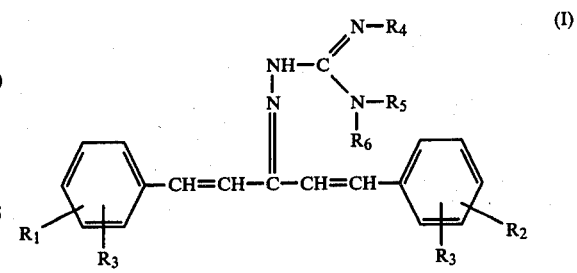

wherein $R_1$ and $R_2$ each represent hydrogen, halogen, $CF_3$, $C_1$-$C_4$ alkyl, $C_1$-$C_4$ alkoxy or $C_1$-$C_4$ alkylthio; $R_3$ is hydrogen or methyl, provided that when $R_3$ is methyl, $R_1$ and $R_2$ is each also methyl; $R_4$ and $R_5$ represent hydrogen or $C_1$-$C_4$ alkyl, and when taken together, an alkylene group of 2 to 6 carbon atoms, methyl or a phenyl alkylene group of 2 to 4 carbon atoms or 1,2-cyclohexylene; and $R_6$ is hydrogen or $C_1$-$C_4$ alkyl; and salts hereof. Preferred compounds for use as grubicidal agents in accordance with this invention are: 1,5-bis-(α,α,α-trifluoro-p-tolyl)-1,4-pentadien-3-one(1,4,5,6-tetrahydro-5,5-dimethyl-2-pyrimidinyl)hydrazone and 1,5-bis-(α,α,α-trifluoro-p-tolyl)-1,4-pentadien-3-one(1,4,5,6-tetrahydro-2-pyrimidinyl)hydrazone.

The compounds of formula-I are particularly useful for controlling the larvae of heel flies in ruminants (i.e., cattle, sheep, goats) when administered orally on a continuing basis as a dietary constituent in feed stuffs containing from 0.005 to 1.0% by weight of the compound. Preferable additions to animal feeds supply the pentadienone hydrazones on a weight basis at levels from 0.025 to 25%. In preparation for incorporation into animal feeds, the active pentadienone hydrazone compounds can be formulated as a premix or supplement containing about 5 to 35% by weight of compound. The remainder of the premix or supplement is usually a mixture of edible feed stufs and animal nutrients, e.g. soybean meal, corn meal, ground grain, fermentation mash solids, vegetable oils and the like. The premix or supplement can be blended with the feed or simply added thereto as a top dressing. The premix or supplement is added to feed stuffs in amounts sufficient to provide the active compound at a concentration which will control cattle grub infestations in susceptible host animals.

For single dose administration the compounds of the invention may be formulated as tablets, pills, boluses, gels, compound resinate or the like, using pharmaceutically acceptable diluents, solvents, resins, binders, lubricants or other similar materials. Among the excipients which may be used are: vegetable gums, magnesium stearate, starch, lactose, dicalcium phosphate and isotonic saline solution.

When the compounds of the invention are administered to the animals in the form of a single topical or oral treatment, a single dose of active compound administered at approximately 0.5 to 250 mg/kg of body weight, and preferably between approximately 5 to 100 mg/kg of body weight, is effective for controlling the heel fly larvae which infest host animals.

The compounds of the invention, as represented by formula-I, may be conveniently formulated as dusts, dust concentrates, wettable powders, or emulsifiable concentrates and applied to host animals by conventional methods (i.e., spraying, dusting, dipping, etc.).

Solid formulations (i.e. dusts) can be prepared by grinding and blending together an inert solid diluent such as attapulgite, kaolin, walnut shell flour, corncob flour, diatomaceous earth or similar material, and the active ingredient when such ingredient is a solid. When the active ingredient is a liquid, it may be sprayed on the carrier and thoroughly mixed therewith, or it may be dissolved in acetone, lower molecular weight alcohols, toluene, xylene, or other similar solvents, and sprayed as a dilute solution on the solid carrier. Dusts usually contain from about 1 to 15% by weight of active ingredient and may be applied at this concentration to host animals and their habitats.

Wettable powders are prepared by grinding together a formula-I compound with an inert solid diluent to achieve a concentration of about 16 to 85% by weight of compound and blending therewith about 5 to 10% by weight of a surfactant. The wettable powder is then generally dispersed in water or other suitable diluent for application as a dilute spray onto the host animal or locus where control is desired or for use as a bath for dipping animal hosts.

Application of various liquid formulations of the formula-I pentadienone hydrazones are generally made with solutions, suspensions or dispersions, containing about 0.005 to 1.0% by weight and preferably 0.005 to 0.5% by weight of formula-I compound.

The larvicidal activity of the compounds of the invention may be conveniently evaluated by a method accepted by the U.S. Agricultural Research Service, in which mice infested with Cuterbra sp. are treated topically with the compounds under evaluation.

The following non-limiting Example further serves to illustrate the invention.

EXAMPLE 1

In Vivo Procedure for Evaluating Larvicidal Activity of Compounds of the Invention Using the Parasite Cuterebra sp. and Mice as Host Animals.

White mice are artificially infested nasally, bucally, or ocularly with 5 newly-hatched larvae of Cuterebra sp. In dermal tests a plastic collar is placed around the neck of each male mouse 48 hours after infection by the parasite, and the portion of the body behind the collar is dipped in 200 ml of an emulsion of a test compound. A standard emulsifiable concentrate consists of 25 parts of test compound, 65 parts of xylene, and 10 parts octylphenoxy polyethoxy ethanol of average molecular weight equal to 628 and having from 9 to 10 ethylene oxide units.

The skin of each mouse is examined carefully for encapsulated live larvae four days after treatment. Effectiveness of the treatments is determined by comparing numbers of larvae encapsulated in treated mice with numbers found in untreated control mice. Usually 3 mice per concentration are treated. If mice or the larvae are killed at the initial concentration of 1%, lower concentrations (0.6, 0.3, 0.2, 0.1% etc.) are tested until there is either no systemic activity or the mice survive.

In oral tests female mice are treated 48 hours after infection by the parasite using a stomach tube consisting of a ½ inch length of polyethylene tubing (ID, 0.034 in.; OD, 0.050 in.) fitted over the end of a 20-gauge needle attached to a 0.25-cc syringe. Mice are individually weighed and dosed with the appropriate amount of a candidate compound formulated in polyoxyethylene (20) sorbitan monolaurate.

Four days after oral treatment the skin of each mouse is examined carefully for encapsulated live larvae. Effectiveness of the treatments is determined by comparing numbers of larvae encapsulated in treated mice with numbers found in untreated control mice. Usually 3 mice per dosage are treated. If the mice or the larvae are killed at the initial dosage of 100 mg/kg, lower dosages (60, 30, 20, 10 mg/kg, etc.) are administered until there is either no systemic activity or the mice survive.

Mortality data are subjected to log-probit analysis in order to determine dosages or concentrations that kill 50 or 90% of the larvae.

The data obtained are presented in Table I below.

TABLE I

In Vivo Evaluation of Compounds of the Invention for the Control of the Parasite Cuterebra sp. Using Mice as Host Animals

| Treatment | Oral Dosage $LD_{50}$ | (mg/kg) $LD_{90}$ | Dermal Dosage $LC_{50}$ | (%) $LC_{90}$ |
|---|---|---|---|---|
| 1,5-bis($\alpha,\alpha,\alpha$-trifluoro-p-tolyl)-1,4-pentadien-3-one(1,4,5,6-tetrahydro-5,5-dimethyl-2-pyrimidinyl)hydrazone | 10.41 | 17.66 | 0.033 | 0.059 |

I claim:

1. A method for protecting ruminant, domestic, and farm animals from infestation by the larvae of flies of the family Hypodermatidae comprising, administering to larvae-infested animals a larvicidally effective amount of a compound having the formula:

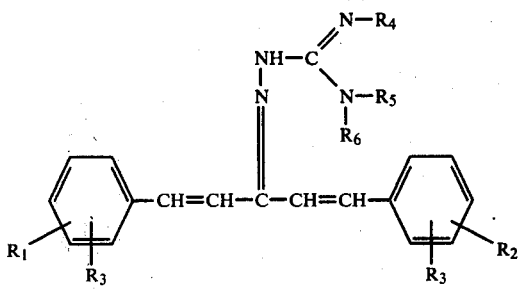

wherein $R_1$ and $R_2$ each is hydrogen, halogen, $CF_3$, $C_1$-$C_4$ alkyl, $C_1$-$C_4$ alkoxy or $C_1$-$C_4$ alkylthio; $R_3$ is hydrogen or methyl, provided that when $R_3$ is methyl, $R_1$ and $R_2$ is each also methyl; $R_4$ and $R_5$ represent hydrogen or $C_1$-$C_4$ alkyl, and when taken together, an alkylene group of 2 to 6 carbon atoms, a methyl substituted or a phenyl substituted alkylene group of 2 to 4 carbon atoms, a dimethyl substituted alkylene group of 2 to 4 carbon atoms or 1,2-cyclohexylene; and $R_6$ is hydrogen or $C_1$-$C_4$ alkyl; or salts thereof.

2. A method according to claim 1 wherein said compound is 1,5-bis(α,α,α-trifluoro-p-tolyl)-1,4-pentadien-3-one(1,4,5,6-tetrahydro-5,5-dimethyl-2-pyrimidinyl)-hydrazone.

3. A method according to claim 1 wherein said compound is 1,5-bis(α,α,α-trifluoro-p-tolyl)-1,4-pentadien-3-one(1,4,5,6-tetrahydro-2-pyrimidinyl)hydrazone.

4. A method according to claim 1 wherein said compound is orally administered to said animals in an edible feed stuff containing from 0.005 to 1.0% by weight of the pentadienone hydrazone compound.

5. A method according to claim 1 wherein said compound is applied to said animal as a topical treatment in an amount sufficient to provide said animal with from about 0.5 to 250 mg/kg of animal body weight of said active compound, wherein said active compound substantially passes through the skin of said animal to provide systemically a larvicidally-effective amount of said active compound.

6. A method according to claim 1 wherein said compound is orally administered to said animal in the form of a single oral dose at a concentration of 0.5 to 250 mg/kg of animal body weight of said compound.

* * * * *